United States Patent [19]

Bjellqvist

[11] Patent Number: 6,090,252
[45] Date of Patent: Jul. 18, 2000

[54] BUFFER SYSTEM FOR ELECTROPHORESIS AND USE THEREOF

[75] Inventor: Bengt Bjellqvist, Stockholm, Sweden

[73] Assignee: Pharmacia Biotech AB, Uppsala, Sweden

[21] Appl. No.: 08/849,287

[22] PCT Filed: Nov. 29, 1995

[86] PCT No.: PCT/SE95/01428

§ 371 Date: May 30, 1997

§ 102(e) Date: May 30, 1997

[87] PCT Pub. No.: WO96/16724

PCT Pub. Date: Jun. 6, 1996

[30] Foreign Application Priority Data

Nov. 30, 1994 [SE] Sweden .................................. 9404141

[51] Int. Cl.[7] .......................... G01N 27/26; G01N 27/447
[52] U.S. Cl. ............................ 204/468; 204/456; 204/606
[58] Field of Search ..................................... 204/456, 457, 204/465, 468, 466, 467, 469, 606, 618

[56] References Cited

U.S. PATENT DOCUMENTS

| | | | |
|---|---|---|---|
| 4,306,956 | 12/1981 | de Castro et al. ...................... | 204/461 |
| 4,415,655 | 11/1983 | de Castro et al. ........................ | 435/17 |
| 4,481,094 | 11/1984 | de Castro et al. ...................... | 204/468 |
| 5,143,646 | 9/1992 | Nochumson et al. .................. | 204/469 |
| 5,578,180 | 11/1996 | Engelhorn et al. ..................... | 204/468 |

FOREIGN PATENT DOCUMENTS 56-6784A1 10/1993 European Pat. Off. .

OTHER PUBLICATIONS

Immobilized pH gradients: New pK values of acrylamido buffers in poly(N–acryloylaminoethoxyethanol) matrices, A Bossi et al., *Electrophoresis*, 1994, 15, 1112–1117.

Hiroko Tamura and Nobuo Ui, "New Buffer System for Disc Electrophoresis Suitable for Slightly Basic Proteins" The Journal of Biochemistry, vol. 71, No. 3 (Mar. 1972) 543–545.

M. Wyckoff et al, "Polyacrylamide Gel Electrophoresis in Sodium Dodecyl Sulfate–Containing Buffers Using Multiphasic Buffer Systems: Properties of the Stack, Valid $R_f$ Measurement, and Optimized Procedure" Analytical Biochemistry, vol. 78, No. 2 (Apr. 1977) 459–482.

*Primary Examiner*—William H. Beisner
*Assistant Examiner*—John S. Starsiak, Jr.
*Attorney, Agent, or Firm*—Birch, Stewart, Kolasch & Birch, LLP

[57] ABSTRACT

A buffer system for conducting discontinuous polyacrylamide gel electrophoresis comprises a separation gel buffer solution, an anodic electrode solution and a cathodic electrode solution. According to the invention, the separation gel buffer contains a base having a pK value of 8.8 or higher and an acid which titrates the pH of the gel buffer to a pH value lower than 8, and the cathodic electrode solution contains an ampholyte or weak acid having a pK value of 9.4 or higher.

18 Claims, 1 Drawing Sheet

BUFFER SYSTEM FOR ELECTROPHORESIS AND USE THEREOF

FIELD OF THE INVENTION

The present invention relates to polyacrylamide gel electrophoresis as a method for separations of proteins, peptides and nucleic acids, and primarily to SDS polyacrylamide gel electrophoresis.

BACKGROUND OF THE INVENTION

Electrophoresis is a widely used procedure for separating charged molecules, such as proteins, peptides, amino acids, nucleic acids and other macromolecules based upon the mobilities of the molecules in an electric field.

Electrophoretic separations are nearly always carried out in gels as supporting medium, the latter serving as molecular sieves that enhance separation. Polyacrylamide gel is frequently used due to its high chemical and mechanical stability. Polyacrylamide gel electrophoresis is often referred to as PAGE.

Proteins and peptides are usually denatured and treated with sodium dodecyl sulphate (SDS), an anionic detergent, prior to the electrophoresis, so-called SDS electrophoresis. Most peptides bind SDS in a constant weight ratio which give them essentially identical charge densities, and their migration velocities in a polyacrylamide gel of suitable porosity are as a consequence related to their molecular weights. Thus, prior to application to the polyacrylamide gel in SDS-electrophoresis, samples are denatured by heating in the presence of excess SDS and a thiol reagent, usually 2-mercaptoethanol or dithiothreitol.

In the earliest publications describing SDS-electrophoresis, continuous phosphate buffers were used (Shapiro, A. L., Vinuela, E., and Maizel, J. V., (1967) Biochem. Biophys. Res. Commun. 28, 815; Weber, K., and Osborne, M., (1969) J. Biol. Chem. 244, 4406). In a continuous buffer system, the same buffer of a chosen pH and ionic strength is used in the gel and in the electrode chambers.

Today, however, the technique is almost solely used with the discontinuous buffer system described in Laemmli, U. K. (1970) Nature (London) 277, 680. In discontinuous systems, the pH of the separation gel normally differs from that of the buffer. The sharpness of the sample zones may be improved by providing a "stacking gel" with higher porosity (lower polymer concentration) and significantly different pH, on top of the separation gel. In the original version used by Laemmli, the high porosity stacking gel contained 0.125 M Tris-Cl buffer, pH 6.8, while the low porosity separation gel contained 0.375 M Tris-Cl buffer, pH 8.8. The electrode reservoirs contained 0.025 M Tris, 0.192 M glycine (pH≈8.3) and 1 gram SDS/liter. When voltage is applied to this system, glycine starts to enter the stacking gel and a sharp boundary (front) will form between a leading chloride-containing zone and a trailing glycine-containing zone. Due to the low ionisation of glycine in the latter zone (resulting pH 8.9), the passage of the front will be accompanied by a drastic increase of voltage, and peptides applied to the top of the stacking gel will concentrate in a narrow very sharp zone behind the front. When the trailing zone enters the separation gel, the pH and the mobility of glycine will increase and simultaneously protein mobilities will decrease due to the lower porosity of the separation gel. With a correctly chosen porosity of the separation gel, peptides of interest will acquire a lower mobility than glycine, "destack" and move in the separation gel with relative velocities mainly determined by their size. In today's practice it is not uncommon to use simplified versions of Laemmli's buffer system. The separation gel buffer may be used as buffer also in the stacking gel, which for a majority of the applications suffice to give sharply stacked peptide zones behind the front. In many cases it is also possible to completely omit the stacking gel and rely solely on the zone sharpening which results within the sample and in connection with sample entrance into the gel. Discussions on the use of Laemmli's discontinuous buffer system can be found in textbooks on electrophoretic techniques (Andrews, A. T., Electrophoresis, Claredon Press, Oxford 1987; Dunn, M. J., Gel electrophoresis: Proteins, Bios Scientific Publisher, Oxford 1993) and detailed experimental protocols are found for example in Ausubel, F. M., et al, Current Protocols in Molecular Biology, Vol. 2, Chapter 10.2, John Wiley & Sons, New York, 1993.

The gels used for stacking and separation, respectively, are normally produced from acrylamide with N,N'-methylene-bisacrylamide (BIS) as a cross-linker, where the BIS concentration normally chosen falls in the range of 2 to 5% by weight of the total monomer concentration. The total monomer concentration used in practice varies between 4 and 20 grams pro 100 ml of gel solution. A number of alternative acrylamide derivatives, such as N,N-dimethyl acrylamide, N-tris(hydroxymethyl)-methylacrylamide and N-hydroxyalkoxyalkyl acrylamide have been suggested to be used instead of acrylamide and there also exist alternative water soluble divinyl compounds, such as N,N'-diallylditartardiamide or N,N'-diacryloylpiperazine, which can be used instead of BIS (U.S. Pat. No. 7,159,847). The polymerization of the gels is normally accomplished with a catalyst system comprised of ammonium persulphate and N,N,N',N'-tetramethylene ethylenediamine (TEMED). Other types of redox initiators for radical polymerization can also be used as well as UV-initiators.

The amide groups in polyacrylamide and most acrylamide derivatives are slowly hydrolysed at the pH of 8.8 used in Laemmli's gel buffer recipe. The hydrolysis proceeds also at low temperature and the carboxylic groups formed are incorporated in the polymer and will generate electro-endosmosis in connection with electrophoresis. The visible effect after 2–3 weeks storage of a gel in a refrigerator prior to electrophoresis is a marked decrease of the distance travelled by the proteins. 3–4 months storage in a refrigerator results in a complete deterioration of the protein separation. Laemmli's buffer system gives excellent results as long as the gels are used shortly after preparation, but it will not give the user reproducible, high quality results when ready-made gels are utilized. The speed of hydrolysis decreases with the hydroxyl ion concentration and in a discontinuous buffer system suitable to combine with ready-made gels for SDS-electrophoresis, the original pH of the gel should not be allowed to exceed 8, and preferably the pH value of the gel should be ≦7.5.

There exist theoretical models describing the concentration, pH and conductivity changes appearing at the moving boundaries generated in electrophoresis with discontinuous buffer systems (Jovin, T. M., 1973, Biochemistry 12, 871–898; Everaets, F. M., Beckers, J. L., and Verheggen, T. P. E. M., Isotachophoresis, Elsevier, Amsterdam, 1976). Computer programs are also available which allow the calculation of the conditions in front of and behind the moving boundary from electrophoretic mobilities and pK values of the compounds constituting the discontinuous buffer system. From information available, a number of discontinuous buffer systems can be defined were the initial pH in the separation gel is well below 8 at the same time as the mobility of leading ion and conductivity in front of the boundary combined with the mobility of trailing ion and conductivity behind the boundary define conditions which concentrate peptides to a sharp, narrow zone in the stacking gel, and in the separation gel give $R_f$-values ($R_f$=distance travelled by peptide divided by the distance travelled by moving boundary) similar to those given by Laemmli's buffer system (Chrambach, A., and Jovin, T. M., 1983, Electrophoresis 4, 190–204).

One such system utilizing 0.112 M Tris-acetate, pH≈6.5, as gel buffer and tricine as trailing ion is used in commercial gels for SDS-electrophoresis. These gels are also utilized for native protein electrophoresis in which case alanine is used as the trailing ion (Phast System Separation Technique File no 110, Pharmacia Biotech AB, Uppsala, Sweden).

U.S. Pat. No. 4,481,094 suggests the use of 2-amino-2-methyl-1,3-propane-diol at pH 6.4–7.3 as gel buffer combined with taurine as trailing ion.

DE-A-41 27 546 describes a buffer system with Tris-formate, pH 7.0–8.5, as gel buffer and taurine as trailing ion, while EP-A-0 509 388 discloses an almost identical buffer system solely differing in that formate is replaced by an anion from the group of acetate, chloride, sulphate and phosphate, and that the useful pH range for the gel buffer is given as 7.0–8.0.

EP-A-0 566 784 describes a buffer system where the gel buffer contains an acid with a pK less than 5, an amine having a pK value between 8 and 8.5, and an ampholyte having a $pK_2$ between 7 and 11 where the ratio of amine to acid should be between 1:0.6 and 1:1 parts by gram equivalent and the ratio of acid to ampholyte between 1:0.5 and 1:4 parts by gram equivalent. Tris is given as the preferred base in the gel buffer as well as in the electrode solutions. Preferred ampholytes in the gel buffer may be selected from the group of glycine, serine, asparagine, α-alanine, N-tris (hydroxymethyl)methyl-3-aminopropanesulphonic acid, tricine and N-tris-(hydroxymethyl)methyl-2-aminoethanesulphonic acid, while the preferred ampholyte in the cathodic electrode solution is glycine or tricine.

While these known approaches give storage stable polyacrylamide gels for SDS-electrophoresis and, in the Tris-acetate/Tris-tricine or Tris-Cl-glycine/Tris-glycine (EP-A-0 566 784) systems, also $R_f$-values similar to those given by Laemmli's buffer system, there are still very notable differences between the resulting band patterns. When pure proteins or standard mixtures are run with the Laemmli system, the result is sharp, well defined bands and the number of stained bands normally agrees with that expected. When the other described buffer systems are used, a number of proteins give broadened and/or diffuse bands and an appreciable number of proteins give extra bands which are generated in connection with the electrophoretic run.

SUMMARY OF THE INVENTION

An object of the present invention is to define discontinuous buffer systems which avoid the generation of artificial extra bands during the electrophoretic separation, result in sharp and well-defined bands of the separated components and at the same time allows the generation of storage stable gels possible to use in SDS electrophoresis.

To achieve the above-mentioned object, the separation gel buffer solution contains a base with pK≧8.8 and an acid which titrates the pH to a value lower than 8 at the same time as the cathodic electrode solution contains an ampholyte or weak acid with a pK value≧9.4.

Other objects and advantages of the invention are apparent from the following description.

DETAILED DESCRIPTION OF THE INVENTION

Figure 1A:
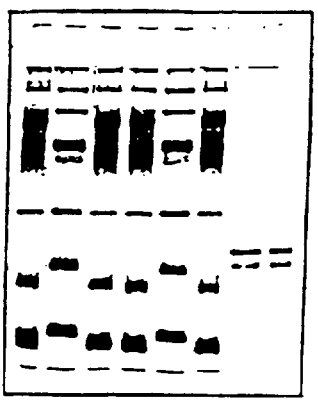
FIGS. 1a to 1h are photographs of separation gels after electrophoretic separations with the buffer systems given in Table 1 below. Samples in FIGS. 1a–1g: Lanes 1 and 6, aged partially oxidised molecular weight markers; lanes 2 and 5, molecular weight markers alkylated with iodoacetamide; lanes 3 and 4, freshly prepared molecular weight markers; lanes 7 and 8, human growth hormone. Samples in FIG. 1h: Lanes 1 and 6, aged partially oxidised molecular weight markers; lanes 2 and 3, molecular weight markers reduced with 1.5% dithiothreitol; lanes 4 and 5, molecular weight markers reduced with 5% mercaptoethanol; lane 7, human growth hormone.

As mentioned above, a critical feature of the present invention is that the gel buffer has a pK≧8.8. All bases with a pK≧8.8 are suitable provided that they do not severely interfere with the formation of a well defined gel to be used in the electrophoretic separation. Examples of suitable bases includes ammonia, primary, secondary and tertiary amines, optionally substituted with alkyl groups, amines containing one or two hydroxyl or ether groups, such as diethanolamine, ethyldiethanolamine, N,N-dimethylethanolamine, N,N-diethylethanolamine, 2-amino-2-methyl-1,3-propanediol, N,N-diethylamino-2,3-propanediol, 2-methyl-2-aminopropanol, and amines containing one amide group, such as N-piperidinopropionamide, N-pyrrolidinopropionamide or N,N-diethylaminopropionamide. Especially suitable bases are amines containing one amide group.

The acid used in the gel buffer solution may be any acid, which at the pH of the gel buffer solution has an electrophoretic mobility higher than that of the fastest moving sample component to be separated and which does not react with acrylamide or interfere with the polymerization reaction. Examples of suitable acids are hydrochloric acid, phosphoric acid, sulphuric acid, formic acid and acetic acid. To avoid hydrolysis of the amide group, the pH of the gel buffer should be lower than 8, and more preferably lower than 7.5.

Non-protonated primary and secondary amines react with acrylamide and acrylamide derivatives and non-protonated tertiary amines interfere with the radical polymerization reaction (Geisthardt, D., and Kruppa, J., (1987) Anal. Biochem. 160, 184–190). In order to get reproducible, well functioning gels for the electrophoretic separation, it is essential that the pH of the gel buffer also meets the requirement to be at least 1 pH unit, and preferably 1.5 pH units below the pK value of the base used in the gel buffer solution.

Without due precautions, as much as 5–10% of the acrylamide may be present unconverted in the polymerized gel. As described in Patterson, S. D., (1994) Anal. Biochem. 221, 1–15, proteins react with unconverted acrylamide in connection with SDS-electrophoresis, but also mercaptoethanol and dithiothreitol react with acrylamide. If appreciable amounts of acrylamide are present, the reducing agent may be consumed at an early stage of the electrophoretic separation. As clarified below, it is in connection with SDS-electrophoresis essential that the reducing agent passes through the gel prior to the passage of the peptides to be separated. For the proper performance of the present invention, it is thus essential that polymerization conditions are used which minimize the amount of acrylamide in the polymerised gel. To thoroughly eliminate oxygen from the solution prior to polymerization is from this point of view highly favourable. If the persulphate-TEMED system is used as polymerization initiator, room temperature polymerization may be used, but generally higher temperatures (40–50° C.) are advantageous. Polymerization with UV-initiators or γ-irradiation are other means to ascertain a high conversion of monomer in the polymerization reaction.

The trailing ion may correspond to a weak acid with $pK \geq 9.4$ or an ampholyte which at the pH developed in the separation zone carries a negative charge less than one and where the pK of the partially neutralised basic group of the ampholyte falls in the range of 9.4–11.0. Examples of suitable ampholytes are glycine, alanine, proline, valine, histidine, lysine, β-alanine, γ-aminobutyric acid and ε-aminocaproic acid. Which acid or ampholyte to choose in each particular case depends on the electrophoretic mobility of the components to be separated and on the pK value of the base included in the gel buffer solution. With proteins and peptides with high electrophoretic mobilities or specifically for SDS-electrophoresis, peptides with molecular weights lower than 10,000 daltons, the ionisation degree of the acid or ampholyte has to be high and the pK value of the weak acid or ampholyte should be lower than or comparable to the pK value of the base. Laemmli's buffer system is suitable for separation of peptides falling in the molecular weight range of about 10 000 to about 300 000 daltons, and for this type of separations the weak acid or ampholyte should have a pK value which is 0.4 to 1.7 pH-units higher than the pK value of the base. Native proteins have lower electrophoretic mobilities than the SDS-peptide complexes, and for native separations it is normally suitable that the pK difference between the acid or ampholyte and the base falls in the range 1–2 pH-units. The $R_f$-values and the molecular weight range covered by the separation can also be influenced by inclusion of the acid or ampholyte present in the cathodic electrode solution in the gel buffer solution. The effect of this inclusion is to decrease the $R_f$-values and to allow peptides with lower molecular weights to be separated than otherwise would have been possible with the chosen ampholyte and base at a given polyacrylamide concentration in the separation gel.

The cathodic electrode solution functions as a source of the trailing ion and in the case of SDS-electrophoresis also as a source for dodecyl sulphate ions. In addition to the acid or ampholyte with a $pK \geq 9.4$ and dodecyl sulphate, the cathodic electrode solution should contain a base. The main object of the base is to supply buffer capacity at the pH of the cathodic electrode solution in order to avoid drastic changes in the ratio of trailing component to dodecyl sulphate supplied to the polyacrylamide gel during the electrophoretic run. The base contained in the gel buffer solution represents one suitable choice, but in reality any base with a $pK \geq 7$ may be used. In many cases Tris is a highly suitable choice.

The anodic electrode solutions serve as a source of the base with $pK \geq 8.8$ present in the gel buffer solution. Besides the base, the anodic electrode solution has to contain a component which titrates the solution either to pH values where the base contributes with buffer capacity or alternatively to pH values falling in the range of 5 to 7. At pH values where the base contributes with buffer capacity, the titrating component may be the acid or ampholyte used in the cathodic electrode solution or any of the acids included in the gel buffer solution. When titration is effected to lower pH values, it is essential that the titrating component has buffer capacity at pH values lower than the pH of the anodic electrode solution and suitable titrants are for example formic and acetic acid.

Polyacrylamide gels are always oxidizing, and this is the case not only when persulphate-TEMED is used as polymerization catalyst, but also when thoroughly deaerated solutions are polymerised with UV-initiators. In SDS-electrophoresis, proteins are reduced in order to break —S—S— bridges prior to sample application. The peptide —SH groups will without due precautions be oxidized during the electrophoretic separation and dimers or internal —S—S— bridges will be formed. In both cases, the result will be a changed electrophoretic mobility of the peptide involved. Oxidation taking place within the stacking gel, when used, will give extra artifactual band in the resulting peptide pattern, while oxidation within the separation gel will result in an increased background between separated peptide bands. Large amounts of thiol are added with the samples on top of the gels to be used in SDS-electrophoresis. The mercaptoethanol concentration used in the standard descriptions is 5%, while the dithiothreitol concentration normally recommended to be used in combination with Laemmli's buffer system is 1.5%. An overlooked, but presumably important feature of Laemmli's buffer system is the high pH in the trailing zone. Mercaptoethanol as well as dithiothreitol will have a higher electrophoretic mobility than glycine and will become stacked behind the rear boundary of the chloride-containing zone. The reducing agents are presumably faster than the SDS-peptide complexes also in the stacking gel and will pass through the polyacrylamide gel in front of the peptides, reduce the oxidizing groups contained in the gel and through this action minimize reoxidation of the thiol groups of the peptide. The plausible explanation to the good quality results achieved with buffer systems according to the present invention is the high pH in the trailing zone, which insures that mercaptoethanol as well as dithiothreitol move through the gel in front of the peptides in the stacking and separation gels. This is not the case for any of the earlier described approaches resulting in storage stable gels for SDS-electrophoresis.

The gel to be used in connection with this invention can be produced by the conventional methods described in the literature. The invention is not restricted to any of the specific geometries used in connection with electrophoresis, but can be adapted to and used with vertical slab gels, horizontal slab gels, vertical rods as well as with capillary geometries.

When electrophoresis is run in slab gels with many samples in parallel, it is generally advisable to avoid a high salt concentration in the samples. Variations in the amount of salt applied with the samples may result in distortions of the electric field during the separation. Normally, high concentrations of mercaptoethanol are used in the samples in connection with SDS-electrophoresis. The mobility of mercaptoethanol is only slightly higher than the mobility of glycine, and in Laemmli's buffer system there is only a marginal conductivity difference between the mercaptoethanol zone and the trailing glycine zone. In this system and buffer system where the mobility of mercaptoethanol is lower than the mobility of the trailing component, variation of the mercaptoethanol load has no consequences when slab gels are used. For buffer systems according to the present invention, no problems appear when the mobility of the trailing component is comparable with or higher than the mobility of mercaptoethanol. For trailing components with low mobility, e.g. β-alanine, γ-aminobutyric acid, ε-aminocaproic acid, comparable amounts of mercaptoethanol have to be applied to the different sample lanes on slab gels if field distortions are to be avoided.

The solution used for polymerization of the gel is, prior to the addition of the polymerization catalysts, storage stable as it has been titrated to pH values where hydrolysis of amide groups is slow and at which neither the amine nor the possible ampholyte contained in the solution will react with acrylamide or acrylamide derivatives. An alternative to ready-made gels is to supply a solution containing all components for producing the gel except the catalyst, which is added by the user prior to pouring the solution into the geometry to be used for the electrophoretic separation. If UV-initiation is used, the UV-initiator may also be included in the solution.

In the Example below, results achieved with buffer systems according to the present invention are compared with results achieved with earlier described buffer systems giving storage stable gels as well as with results with Laemmli's buffer system. The purpose of the Example is to clearly illustrate the advantages obtained, and it is in no way intended to limit the scope of the present invention.

EXAMPLE 1

For the experiment described below, small conventional units for vertical slab gel electrophoresis were used. The equipment allowed two gels to be run in parallel. The spacers used were 0.75 mm thick and the gels were cast between a notched and a plain glass plate of the size 105 mm×100 mm. 80 mm high separation gels were cast from solutions containing 12.125 g acrylamide/100 ml, 0.375 g BIS/100 ml and with the buffer compositions indicated in Table 1.

Figure 1B:
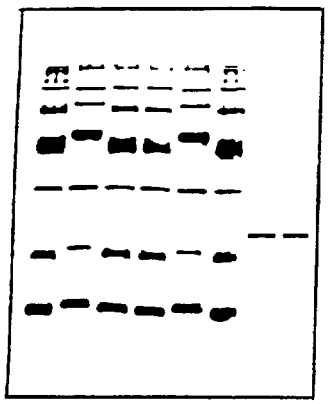
Figure 1C:
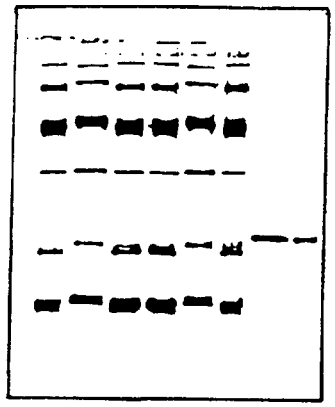
Figure 1D:
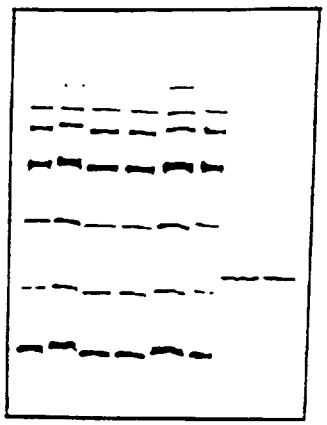
Figure 1E:
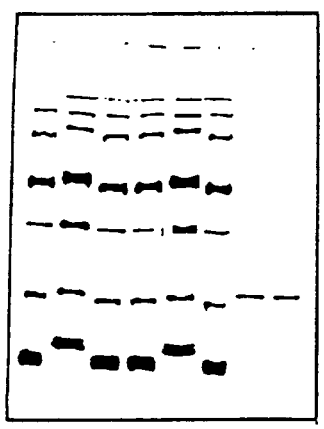

Buffer systems combining Tris and taurine as described in DE-A-41 27 546 and EP-A-0 509 388 do not give patterns comparable with those resulting with the Laemmli buffer system. Taurine has been included in the gel buffer of the system accounted for in FIG. 1b to compensate for this difference. Buffer systems combining 2-amino-2-methyl-1, 3-propane-diol and taurine can not be adjusted to give results comparable with Laemmli's buffer systems and the comparison with the buffer system described in the aforementioned U.S. Pat. No. 4,481,094 has for this reason been omitted.

Figure 1F:
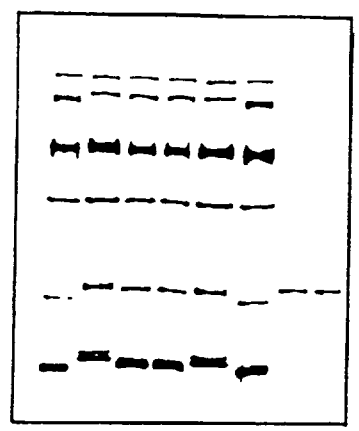

The gel shown in FIG. 1f was polymerised with the aid of a water soluble UV-initiator; for all other gels chemical polymerization was used. Prior to polymerization, the solutions were thoroughly freed from oxygen by nitrogen bubbling. 250 ppm ammonium persulphate and 250 ppm TEMED were added as polymerization catalysts. The separation gels were cast under nitrogen protection and allowed to polymerise for 30–60 minutes at room temperature. 20 mm high stacking gels were then cast on top of the separation gel. The stacking gels contained 3.88 g acrylamide and 0.12 g Bis/100 ml solution and had the same buffer composition as the corresponding separation gels. 500 ppm persulphate and 500 ppm TEMED were used as catalysts. 10 mm deep and 6 mm wide sample application slots were generated with the aid of a plastic comb put into position prior to the onset of gel formation.

The samples used were a commercial molecular weight marker mixture (Table 2) and human growth hormone. Freshly prepared samples were solubilised in 0.375 M Tris-Cl solution pH 8.8, containing 5% β-mercaptoethanol, 10% SDS, 5% glycerol and 0.05% bromophenol blue. Sample solutions were brought to 95° C. for 4 minutes. Samples were also made in which mercaptoethanol was replaced by 1.5% dithiothreitol. Besides the fresh samples, two earlier prepared samples were used. The solution added prior to the reduction at 95° C. contained 1% dithiothreitol and the reduction was performed at a 5 times higher protein concentration. After reduction, a part of the sample was diluted 5 times with a solution containing sample buffer, SDS, glycerol and bromophenol blue but no reducing agent. Another part of the reduced solution was diluted 5 times with a solution containing sample buffer, SDS, glycerol, bromophenol blue and 1% iodoacetamide. These samples were stored in a freezer (−16° C.) and used repeatedly. Iodoacetamide alkylates the —SH groups of the proteins and in this manner protects against formation of —S—S— bridges. The electrophoretic mobilities of the alkylated peptides are identical or slightly lower than the mobilities of the corresponding reduced peptides.

Prior to the electrophoresis, the plastic combs were taken out from the gels, and the gels were mounted in the equipment. The anodic and cathodic electrode chambers were filled with the solutions specified in Table 1. 4 μl samples were added to the sample slots through the upper cathodic electrode solution. The experiments were run with 30 mA constant current (two gels) and were broken as the bromophenol blue line reached the bottom edge of the gel.

Proteins were fixed in a 40% ethanol, 10% acetic acid solution (30 minutes). The gels were then incubated in a solution containing 30% ethanol, sodium acetate, sodium thiosulphate and glutardialdehyde for 60 minutes, washed 3×5 minutes in water, incubated in a silver nitrate solution (40 minutes) and developed in a sodium carbonate solution containing 0.01% formaldehyde.

Figure 1G:
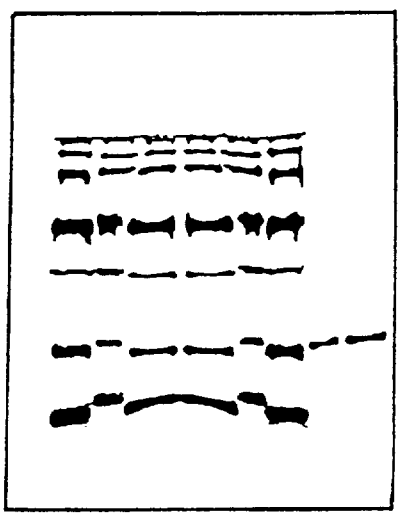
Figure 1H:
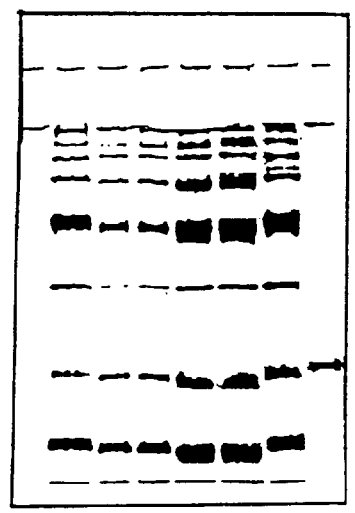

The resulting developed gels are shown in FIGS. 1a–1g. The figures are arranged so that the resulting pH values in the trailing zones increase in the order from FIG. 1a to FIG. 1g. In the Tris-acetate/Tris-tricine system (FIG. 1a) with a trailing zone of pH≈8.1, human growth hormone gives an extra band and bovine serum albumin, ovalbumin and the soybean trypsin inhibitor are also drastically influenced. Of the uninfluenced peptides, bovine carbonic anhydrase is known not to contain any —SH groups. In the Tris-acetate-taurine/Tris-taurine system (FIG. 1b), the effects on serum albumin and ovalbumin are still present but less pronounced. The trypsin inhibitor is completely oxidized. In the Tris-chloride-glycine/Tris-glycine system (FIG. 1c), the trypsin inhibitor is oxidized. Dithiothreitol has a higher electrophoretic mobility than mercaptoethanol in the Tris-chloride-glycine/Tris-glycine system, and FIG. 1h has been included to illustrate the difference appearing with a reducing agent which has an electrophoretic mobility higher than the mobility of the antitrypsin inhibitor. With Laemmli's buffer system (FIG. 1d) as well as with buffer systems according to the present invention (FIGS. 1e–1g), all peptides are maintained in their reduced forms. With β-alanine as trailing component, the differences in mercaptoethanol applied with the samples created marked electric field distortions as can be seen in FIG. 1g.

TABLE 1

Composition of buffer systems used in Example 1

| FIG. | Gel buffer | Anodic electrode solution | Cathodic electrode solution |
|---|---|---|---|
| 1a | 0.112M Tris, 0.112M acetate, pH = 6.5 | 0.05M Tris, 0.05M acetate | 0.021M Tris, 0.021M tricine, 1.5 gram SDS/liter |
| 1b | 0.0625M Tris, 0.0625M taurine, HAc added to get pH = 6.5 | 0.05M Tris, 0.05M acetate | 0.032M Tris, 0.058M taurine, 1.5 gram SDS/liter |
| 1c and 1h | 0.074M Tris, 0.0625M chloride, 0.15M glycine, pH = 7.3 | 0.025M Tris, 0.192M glycine | 0.025M Tris, 0.192M glycine, 1.0 gram SDS/liter |
| 1d | 0.375M Tris, 0.0625M chloride, pH = 8.8 | 0.025M Tris, 0.192M glycine | 0.025M Tris, 0.192M glycine, 1.0 gram SDS/liter |
| 1e | 0.0625M 3-piperidino-propionamid (PPA), HCl added to get pH = 6.5 | 0.05M PPA, 0.05M acetate | 0.025M Tris, 0.192M glycine, 1.0 gram SDS/liter |
| 1f | 0.0625M N,N-dimethyl-aminoethanol (DMAE), HCl added to get pH = 6.5 | 0.05M DMAE, 0.05M acetate | 0.025M Tris, 0.192M glycine, 1.0 gram SDS/liter |
| 1g | 0.0625M 2-amino-2-methyl-propanol (AMP), HCl added to get pH = 6.5 | 0.05M AMP, 0.05M acetate | 0.10M Tris, 0.192M β-alanine, 1.0 gram SDS/liter |

TABLE 2

Proteins in molecular weight marker mixture

| Protein | Subunit molecular weight | Source |
|---|---|---|
| phosphorylase b | 94000 | rabbit muscle |
| albumin | 67000 | bovine serum |
| ovalbumin | 43000 | chicken egg |
| carbonic anhydrase | 30000 | bovine erythrocyte |
| trypsin inhibitor | 20100 | soybean |
| α-lactalbumin | 14400 | bovine milk |

I claim:

1. A buffer system for conducting discontinuous polyacrylamide gel electrophoresis, comprising a separation gel buffer solution, an anodic electrode solution and a cathodic electrode solution, characterized in that the separation gel buffer contains a base having a pK value of 8.8 or higher, and an acid which titrates the pH of the gel buffer to a pH value lower than 8, and that the cathodic electrode solution contains an ampholyte or weak acid having a pK value of 9.4 or higher.

2. The buffer system according to claim 1, characterized in that the pH value of the separation gel buffer is at least one pH unit below the pK value of said base.

3. The buffer system according to claim 1 or 2, characterized in that the pH value of the separation gel buffer is lower than 7.5.

4. The buffer system according to claim 1, characterized in that the anodic electrode solution contains said base having a pK value of 8.8 or higher.

5. The buffer system according to claim 4, characterized in that the anodic electrode solution additionally contains a component which titrates the electrode solution to a pH value where the base present therein contributes with buffer capacity, or to a pH value in the range of about 5 to about 7.

6. The buffer system according to claim 1, characterized in that the cathodic electrode solution contains a base having a pK value of 7 or higher.

7. The buffer system according to claim 1, characterized in that the separation gel buffer has included therein said weak acid or ampholyte present in the cathodic electrode solution.

8. The buffer system of claim 5 for separation of proteins and peptides of molecular weights less than 10,000 daltons, characterized in that said component in the anodic electrode solution has a pK value lower than or approximately equal to the pH value of said base in the separation gel buffer solution.

9. The buffer system according to claim 1 for separation of proteins and peptides of molecular weights in the range of about 10,000 to about 300,000 daltons, characterized in that said weak acid or ampholyte in the cathodic electrode solution has a pK value which is from about 0.4 to about 1.7 pH units higher than the pK value of said base in the separation gel buffer solution.

10. The buffer system according to claim 1, further comprising a sample that has been treated with sodium dodecyl sulfate.

11. The buffer system according to claim 1 for separation of native proteins and peptides, characterized in that the pK value of said weak acid or ampholyte in the cathodic electrode solution is from about 1 to about 2 pH units higher than the pK value of said base in the separation gel buffer solution.

12. The buffer system according to claim 1, characterized in that said base in the separation gel buffer solution is selected from ammonia, primary, secondary and tertiary amines, optionally substituted with alkyl groups, amines containing one or two hydroxyl groups, and amines containing an amide group.

13. The buffer system according to claim 12, characterized in that said base in the separation gel buffer solution is selected from diethanolamine, ethyldiethanolamine, N,N-dimethylethanolamine, N,N-diethylethanolamine, 2-amino-2-methyl-1,3-propanediol, N,N-diethylamino-2,3-propanediol, 2-amino-2-methylpropanol, N-piperidinopropionamide, N-pyrrolidinopropionamide and N,N-diethylaminopropionamide.

14. The buffer system according to claim 1, characterized in that said ampholyte in the cathodic electrode solution is selected from glycine, alanine, proline, valine, histidine, lysine, β-alanine, γ-aminobutyric acid and ε-aminocaproic acid.

15. The buffer system according to claim 1, characterized in that said acid in the separation gel buffer solution is selected from hydrochloric acid, phosphoric acid, sulphuric acid, formic acid and acetic acid.

16. A method of conducting discontinuous polyacrylamide gel electrophoresis, characterized by using a buffer system according to claim 1, comprising the steps of:

1) adding a sample containing macromolecules to a polyacrylamide gel support medium;

2) contacting the polyacrylamide gel support medium containing said sample to the gel buffer solution; and 3) subjecting the sample and the polyacrylamide gel support medium to differential electrical potential to produce migration of the macromolecules.

17. A method of conducting discontinuous polyacrylamide gel electrophoresis, characterized by using a buffer system according to claim 1, comprising the steps of:

1) treating a sample containing macromolecules with sodium dodecyl sulfate;

2) adding the sodium dodecyl sulfate treated sample of step 1) to a polyacrylamide gel support medium;

3) contacting the polyacrylamide gel support medium containing said treated sample to a gel buffer solution; and 4) subjecting said treated sample and the polyacrylamide gel support medium to differential electrical potential to produce migration of the macromolecules.

18. The buffer system according to claim 2, characterized in that the pH value of the separation gel buffer is at least 1.5 pH units below the pK value of said base.

* * * * *